US010501576B2

(12) United States Patent
Gnanou et al.

(10) Patent No.: US 10,501,576 B2
(45) Date of Patent: Dec. 10, 2019

(54) USE OF CO2 FOR THE SYNTHESIS OF CYCLIC GLYCOCARBONATES AND LINEAR POLYGLYCOCARBONATES BY POLYCONDENSATION FROM GLYCANS

(71) Applicant: King Abdullah University of Science and Technology, Thuwal (SA)

(72) Inventors: Yves Gnanou, Thuwal (SA); Debasis Pati, Thuwal (SA); Xiaoshuang Feng, Thuwal (SA); Nikolaos Hadjichristidis, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 112 days.

(21) Appl. No.: 15/566,473

(22) PCT Filed: Apr. 13, 2016

(86) PCT No.: PCT/IB2016/052108
§ 371 (c)(1),
(2) Date: Oct. 13, 2017

(87) PCT Pub. No.: WO2016/166682
PCT Pub. Date: Oct. 20, 2016

(65) Prior Publication Data

US 2018/0118884 A1 May 3, 2018

Related U.S. Application Data

(60) Provisional application No. 62/146,723, filed on Apr. 13, 2015.

(51) Int. Cl.
*C07H 1/00* (2006.01)
*C07H 13/12* (2006.01)
(Continued)

(52) U.S. Cl.
CPC ............ *C08G 64/323* (2013.01); *C07H 1/00* (2013.01); *C07H 13/12* (2013.01); *C08G 64/0208* (2013.01)

(58) Field of Classification Search
None
See application file for complete search history.

(56) References Cited

U.S. PATENT DOCUMENTS 4,826,952 A * 5/1989 Kuyper .................. C08G 18/44 528/371
4,826,953 A * 5/1989 Kuyper .................. C08G 18/44 528/371

(Continued)

FOREIGN PATENT DOCUMENTS

| | | | |
|---|---|---|---|
| WO | 2008057263 | A2 | 5/2008 |
| WO | 2012051448 | A1 | 4/2012 |
| WO | 2013036863 | A2 | 3/2013 |

OTHER PUBLICATIONS

Isocyanate and Phosgene Free Routes to Polyfunctional Cyclic Carbonates and Green Polyurethanes by Fixation of Carbon Dioxide, to Blattman et al., Macromol. Rapid Comm. 2014, 35, 1238-1254 (Year: 2014).*

(Continued)

*Primary Examiner* — Peter A Salamon
(74) *Attorney, Agent, or Firm* — Billion & Armitage; Lisbeth C. Robinson

(57) ABSTRACT

Provided herein are methods for synthesizing cyclic carbonates, glycocarbonates, and polyglycocarbonates by reacting polyol glycans with carbon dioxide. Synthesis can include selective polycondensation of polyol glycan hydroxyl moieties.

20 Claims, 15 Drawing Sheets

(51) Int. Cl.
*C08G 64/32* (2006.01)
*C08G 64/02* (2006.01)

(56) References Cited

U.S. PATENT DOCUMENTS

| | | | | |
|---|---|---|---|---|
| 2011/0046301 | A1* | 2/2011 | Mignani | B01J 31/006 524/590 |
| 2018/0062766 | A1 | 3/2018 | Ooi et al. | |
| 2018/0118884 | A1* | 5/2018 | Gnanou | C07H 1/00 |

OTHER PUBLICATIONS

Synthesis of isosorbide based polyurethanes: An isocyanate free method, to Besse et al., Reactive & Functional Polymers 73 (2013 ) 588-594 (Year: 2013).*

Controlled synthesis of polyepichlorohydrin with pendant cyclic carbonate functions for free polyurethane networks, to Brocas et al., Journal of Polymer Science Part A: Polymer Chemistry, 2011, 2677-2684. (Year: 2011).*

Blattmann, et aL, "Isocyanate-and Phosgene-Free Routes to Polyfunctional Cyclic Carbonates and Green Polyurethanes by Fixation of Carbon Dioxide", Macromolecular Rapid Communications, vol. 35, No. 14, Jul. 30, 2014, 1238-1254.

Habba, et aL, "Synthesis of Polycarbonate From Dimethyl Carbonate and Bisphenol-A-Through a non-Phosgene Process", Journal of Polymer Science, Polymer Chemistry Edition, Interscience Publishers, New York, NY, US, vol. 37, No. 13, Jul. 1, 2099, 2087-2093.

Search Report and Written Opinion for PCT/IB2016/052108, dated Jul. 11, 2016.

Suriano, et al. "Synthesis of a family of amphiphilic glycopolymers via controlled ring-opening polymerization of runctionalized cyclic carbonates and their application in drug delivery" Biomaterials 2010, 2637-2645.

Gustafson, et al., "Poly(D-glucose carbonate) Block Copolymers: A Platform for Natural Product-Based Nanomaterials with Solvothermatic Characteristics", Biomacromolecules, 14, 2013, 3346-3353.

Haba, et al., "Anionic Ring-Opening Copolymerization of L-Lactide with a Five-Membered Cyclic Carbonate Having a Glucopyranoside Structure", Polymer Journal, vol. 41, No. 9, 2009, 702-708.

Haba, et al., "Anionic Ring-Opening Polymerization of Methyl 4,6-O-Benzylidene-2-3-O-carbonyl-a-Dglucopyranoside: A First Example of Anionic Ring-Opening Polymerization of Five-Membered Cyclic Carbonate without Elimination of CO2", Macromolecules, 38, 2005, 3562-3563.

Komura, et al., "Preparation of cyclic carbonates of sugar derivatives with some carbonylating agents*", Research, 40, 1975, 391-395 Carbohydrate.

Lim, et al., "Metal-Free Synthesis of Cyclic and Acyclic Carbonates from CO2 and Alcohols", Eur. J. Org. Chem., 2014, 1823-1826.

Mikami, et al., "Polycarbonates Derived from Glucos via an Organocatalytic Approach", J. Am. Chem. Soc., 135, 2013, 6826-6829.

Sanders, et al., "A Simple and Efficient Synthesis of Functionalized Cyclic Carbonate Monomers Using a Versatile Pentafluorophenyl Ester Intermediate", J. Am. Chem. Soc., 132, 2010, 14724-14726.

* cited by examiner

USE OF CO2 FOR THE SYNTHESIS OF CYCLIC GLYCOCARBONATES AND LINEAR POLYGLYCOCARBONATES BY POLYCONDENSATION FROM GLYCANS

This application is a National Stage Application of PCT/IB2016/052108, filed on Apr. 13, 2016, which claims benefit of Application No. 62/146,723, filed on Apr. 13, 2015 in the United States of America and which applications are incorporated herein by reference. A claim of priority to all, to the extent appropriate, is made.

BACKGROUND

Polycarbonates comprise a broad class of durable materials widely used both as commodity plastics and engineering plastics due to a number of advantageous features including temperature resistance, impact resistance and optical properties. Polycarbonates are utilized throughout the electronics, construction, data storage, automotive, aeronautical, security, medical and telecommunications industries, among others. Polycarbonates are primarily synthesized from bisphenol A (BPA) and phosgene, which account for an annual production of about 1 billion kilograms. Many other polycarbonate synthesis mechanisms exist, with the underlying commonality being a synthetic scheme involving a diol (i.e., a compound comprising two hydroxyl groups, or polyol, and phosgene, phosgene derivatives, or isocyanates.

All such synthetic methods are detrimental to the environment and the health and safety of workers due to the toxic nature of the phosgene, phosgene derivatives, and isocyanates. Further, BPA is a harmful pollutant, even in spite of its low soil half-life, and has been linked to numerous adverse health effects.

SUMMARY

In general, this disclosure describes synthesis of cyclic glycocarbonates and linear polyglycocarbonates from glycans using carbon dioxide ($CO_2$). In particular, this disclosure describes synthesis of cyclic glycocarbonates from mannose, galactose monosaccharide and lactose disaccharides, and synthesis of linear polyglycocarbonates from glucose. Also demonstrated herein is selective polycondensation of various glucose derivatives to produce the linear polyglycocarbonates.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1:
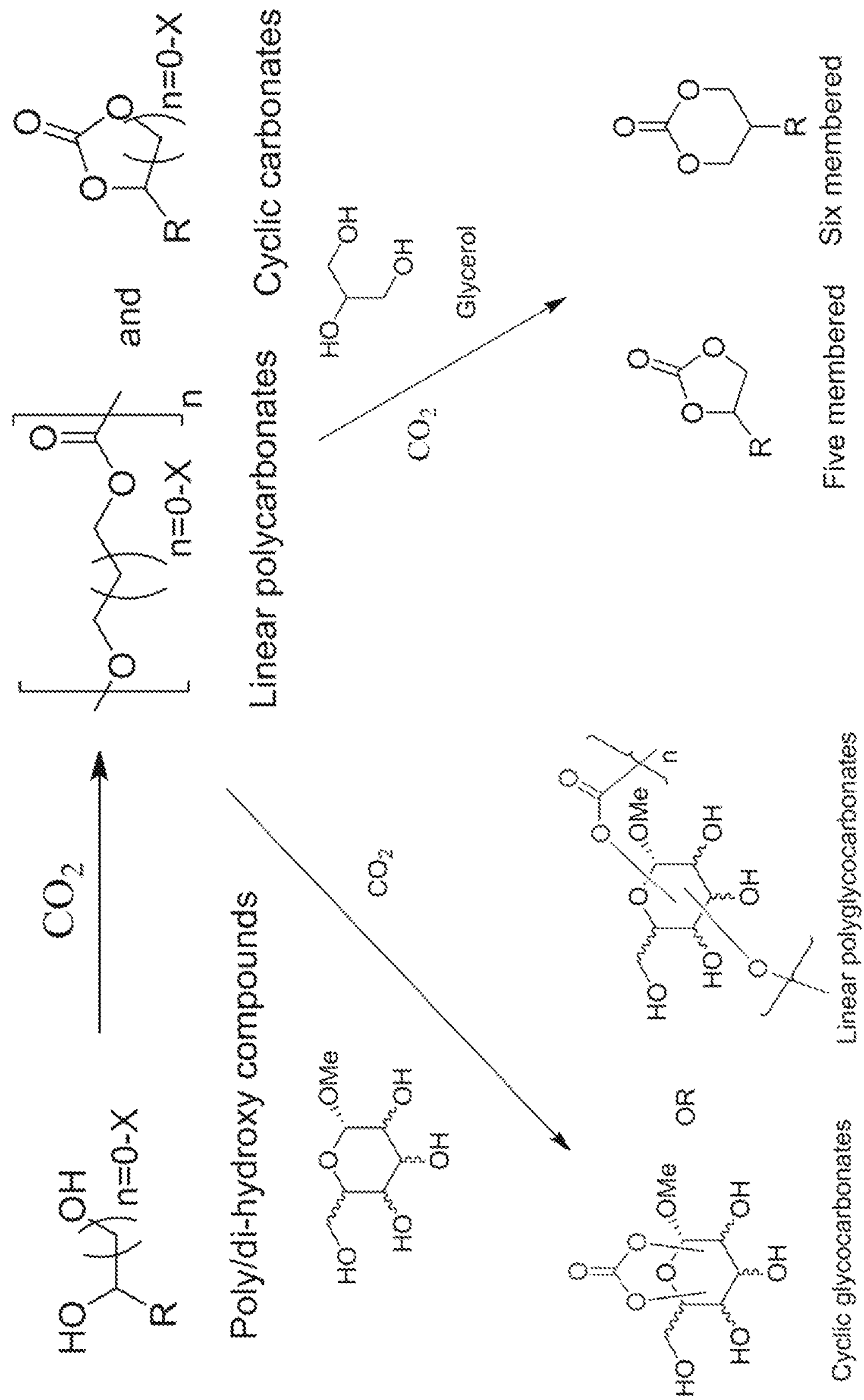
FIG. 1 illustrates an overview of green synthesis of cyclic or linear polycarbonates directly from $CO_2$, according to one or more embodiments of this disclosure.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The methods and compositions disclosed herein provide an alternative to conventional methods for synthesizing cyclic carbonates, glycocarbonates, and polyglycocarbonates, which use toxic phosgene, phosgene derivatives or isocyanates and synthetic reagents. There exists a need for environmentally friendly processes for synthesizing cyclic carbonates and/or glycocarbonates—which have a detrimental effect on environment and when used for the large-scale production. In particular, this disclosure provides novel methods for synthesizing cyclic carbonates, glycocarbonates, and polyglycocarbonates using $CO_2$. Further disclosed herein are novel methods for synthesizing cyclic carbonates, glycocarbonates, and polyglycocarbonates using naturally occurring glycans. The ability to use naturally occurring glycans as synthesis reactants offers the opportunity to obviate environmental and safety hazards germane to synthetic reagents, while also providing a more cost effective alternative.

As used herein, "polycarbonates" refers to a general class of monomers and polymers containing a carbonate moiety.

As used herein, "polyol" refers to a compound comprising two or more hydroxyl groups. An example of a polyol includes bisphenol A (BPA), among many others.

As used herein, "hexose" generally refers to a class of monosaccharides characterized by six carbon atoms and a chemical formula of $C_6H_{12}O_6$. Hexoses having an aldehyde functional group at position 1 are classified as aldohexoses, whereas hexoses having a ketone functional group at position 2 are classified as ketohexoses. Aldohexoses include four chiral centers allowing for 16 stereoisomers, or 8 pairs of L-/D-enantiomers. The 8 aldohexose enantiomer pairs include allose, altrose, galactose, glucose, gulose, idose, mannose, and talose. Hexose molecules are polyols. In both open chain and heterocyclic, hemiacetal aldohexoses, the L-/D-distinction is determined by the orientation of the hydroxyl group at position 5. For example, open-chain D-Galactose and L-Galactose have the following structures:

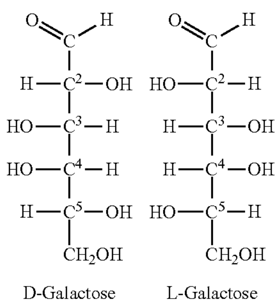

Open-chain aldohexoses can convert to heterocylic forms upon nucleophillic addition between the aldehyde function group at position 1 the hydroxyl group at position 4 or position 5. A reaction at position 4 yields α and β steriosiomsers of furanose, a five-membered cyclic, wherein the α and β stereoisomers are differentiated by the hydroxyl orientation at the anomeric carbon. For example, α-D-Galactofuranose has the following structure:

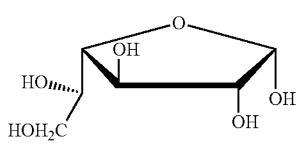

while β-D-Galactofuranose has the following structure:

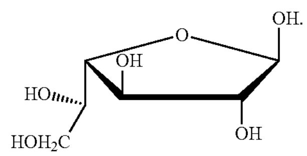

Reaction at position 5 yields α and β sterioisomers of pyranose, a six-membered cyclic, wherein the α and β stereoisomers are differentiated by the hydroxyl orientation at the anomeric carbon. For example, α-D-Galactopyranose has the following structure:

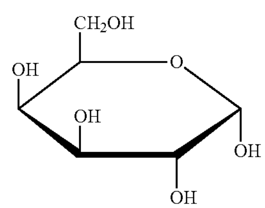

while β-D-Galactopyranose has the following structure:

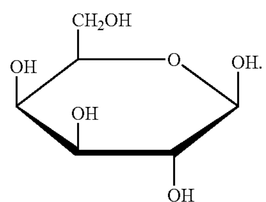

Converting the anomeric hydroxyl group of a pyranose molecule to an $OC_n$ group forms a pyranoside. For example, D-β-methyl galactopyranoside has the following structure:

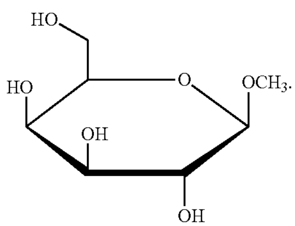

In another example, open-chain D-mannose has the following structure:

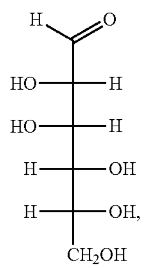 [SMILES: O=CC(O)C(O)C(O)C(O)CO]

while heterocyclic α-D-Mannopyranose has the following structure:

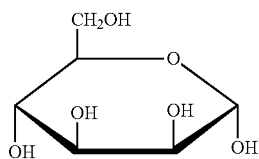

and heterocyclic β-D-Mannopyranose has the following structure:

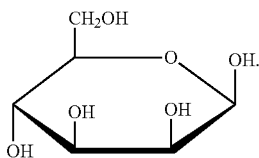

In another example, open-chain D-glucose has the following structure:

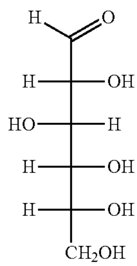

while heterocyclic α-D-Glucopyranose has the following structure:

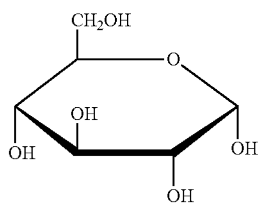

and heterocyclic β-D-Glucopyranose has the following structure:

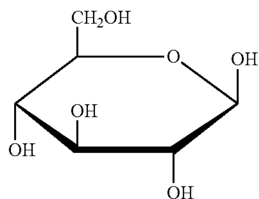

As used herein, the term "glycan", or the prefix "glyco-" refers to a molecule containing one or more saccharide moieties. Similarly, the term "glycoside" refers to any molecule in which a saccharide group, or glycone, is bonded through its anomeric carbon to another group, or a glycone, via a glycosidic bond. The glycone can comprise one or more saccharide groups. The glycosidic bond can be formed by oxygen, nitrogen, or carbon. Hexose, as described above, constitutes a class of glycosides. In another example, D-β-methyl galactopyranoside and D-lactose are glycopyranosides.

Lactose refers to a disaccharide comprising galactose and glucose moieties. An example of lactose is lactopyranose, which is formed via glycosidic bonding between β-galactopyranose and the 4 position of α-glucopyranose and/or β-glucopyranose. Accordingly, "α-lactose" and "β-lactose" refer to anomeric form of the glucopyranose ring. For example, β-lactose has the following structure:

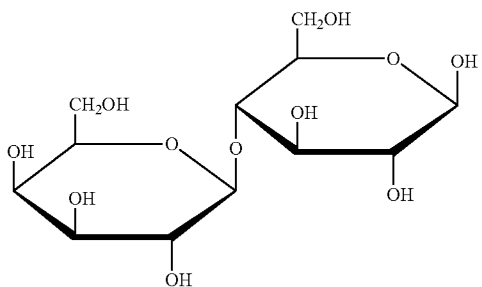

The glycosidic bonding of β-galactopyranose with glucopyranose classifies lactose as a pyranoside.

FIG. 1 illustrates a non-limiting overview of green synthesis of cyclic or linear polycarbonates directly from $CO_2$. As provided herein, methods for synthesizing glycocarbonates can comprise reacting a polyol glycan with carbon dioxide. A polyol can comprise 2 hydroxyl, groups, 3 hydroxyl groups, 4 hydroxyl groups, 5 hydroxyl groups, or more than 5 hydroxyl groups. In some embodiments, two hydroxyl groups which form the carbonate moiety are substituents of adjacent carbons atoms of the polyol glycan. In some such embodiments, the two hydroxyl groups are cis relative to each other. In other such embodiments, the two hydroxyl groups are trans relative to each other. In some embodiments, two hydroxyl groups which form the carbonate moiety are substituents of non-adjacent carbon atoms of the polyol glycan. In some such embodiments, the two hydroxyl groups are cis relative to each other. In other such embodiments, the two hydroxyl groups are trans relative to each other.

The glycan can comprise an open chain or closed chain structure. In some embodiments, the polyol glycan can comprise hexose. In other embodiments, the polyol glycan can comprise a pyranose moiety. In some such embodiments, the polyol glycan can comprise a polysaccharide moiety. In other embodiments, the polyol glycan can comprise a pyranoside. In some embodiments, the glyan can comprise a monosaccharide, disaccharide, oligosaccharide, or polysaccharide.

In some embodiments, the polyol glycan can comprise glycan derivatives. Glycan derivatives can include α-Methyl 3 and 4 di-O-methyl 2 and 6 dihydroxyls glucopyranoside, α-Methyl 2 and 4 di-O-methyl 3 and 6 dihydroxyls glucopyranoside, and other like saccharides, including disaccharides and trisaccharides.

In some embodiments, reacting can occur in the presence of one or more solvents. A non-limiting list of suitable solvents can include dibromomethane, dimethylformamide, ionic liquids, or combinations thereof. Further examples of solvents include ethers, such as triglycol dimethyl ether, tetrahydrofuran and dimethyl sulfoxide. An example of a suitable ionic liquid includes 1-Butyl-3-methylimidazolium hexafluorophosphate. Additionally, ionic liquids can include Imidazolium based ionic liquids with different counter ions, such as 3-Methyl-(4-9)-(fluoro)imidazolium Bis[(trifluoromethyl)sulfonyl]imide, 1-hexyl-3-methylimidazolium tris (penta fluoro propyl)trifluoro phosphate and 1-pentyl-3-methyl imidazolium tris(nona fluoro butyl)]trifluorophosphate etc. Ionic liquids can include ammonium based ionic liquids with different counter ions, such as choline bis(trifluoromethylsulfonyl)imide, tetrabutyl ammonium docusate, peg-5-cocomonium methylsulphate etc. (ref: J. Phys. Chem. B, Vol. 111, No. 30, 2007). A further example of ionic liquids includes super based derived protonic ionic liquids, such as Methyl-triaza bicycloundacane (MTBD) and trifluoroethanol [MTBDH+] [TFE-] (ref: Angew. Chem. Int. Ed. 2010, 49, 5978-5981). Examples of ionic liquids include polyionic liquids, such as poly(1-[(2-methacryloyloxy) ethyl]-3-butylimidazoliums, poly(1-ethyl-3-vinyl-imidazolium) bis(trifluoromethylsulfonyl)imide, N,N-dimetyl-N,N-diallylammonium bis(trifluoromethylsulfonyl)imide and poly(diallyldimethylammonium chloride) solution (Electrochimica Acta, doi:10.1016/j.electacta.2015.03.038)].

In some embodiments, reacting can be conducted in the presence of a catalyst. A non-limiting list of suitable catalysts can include 1,8-diazabicyclo[5.4.0]undec-7-ene. Further examples of catalysts include carbene, phosphagene bases and earth metal salts (LiCl, LiBr, LiOTf, $LiPF_6$ etc.). Further, methods as provided herein are free of phosgene, phosgene derivatives, and isocyanates.

In some embodiments, reacting occurs at a pressure between about 1 bar and about 20 bar. In other embodiments, reaction occurs at a pressure between about 2.5 bar and about 15 bar. In other embodiments, reacting occurs at a pressure between about 5 bar and about 10 bar. In some embodiments herein, reacting can occur between about 60° F. and about 80° F., between about 65° F. and about 75° F. In some embodiments, reacting occurs at room temperature, or about 68° F. In other embodiments, reacting can occur at about 70° F. In some embodiments, reacting occurs over a period of about 12 hours, about 24 hours, about 36 hours, about 48 hours, about 60 hours, about 72 hours, about 84 hours, or about 96 hours.

In some embodiments, methods further comprises selectively protecting one or more hydroxyl moieties of the polyol glycan before reacting, wherein the polyol glycan comprises at least three hydroxyl moieties. The number of protected hydroxyl moieties can be selected such that two hydroxyl moieties remain unprotected. For example, two hydroxyl moieties of a polyol glycan having four hydroxyl moieties can be protected before reacting. Protecting can include methylating.

In some embodiments, cyclic and linear polyglycocarbonates can be obtained via cyclization and/or polycondensation by reacting commercially available D-α-methyl mannose, galactose monosaccharides, D-Lactose disaccharides and glucose with organo base diazabycyclo undecene (DBU) and $CO_2$.

In other embodiments, cyclic glycocarbonates and linear polyglycocarbonates can be synthesized from glycans through reaction with $CO_2$. In one such embodiment, cyclic glycocarbonates can be synthesized from mannose and galactose monosaccharides and lactose disaccharides by cyclization of their cis dihydroxyls (e.g., 2 & 3 cis-dihydroxyls in mannose, 3 & 4 cis-dihydroxyls in galactose and lactose). In other embodiments, linear polyglycocarbonates can be synthesized from glucose by polycondensation of the alternate trans (2, 3 and 4) hydroxyls with $CO_2$. In other embodiments, linear polyglycocarbonates can be synthesized by selective polycondensation of various glucose derivatives by selectively leaving two hydroxyls free and protecting one or more remaining hydroxyl groups. In some embodiments cyclic glycocarbonates can be conjugated to amine/thiol functionalized materials to increase their hydrophilicity and glycans specificity towards biological recognitions.

The synthesis methodology described herein can further be extended to the other polyhydroxyls compounds to synthesize cyclic carbonates or linear polycarbonates.

EXAMPLES

Example 1: Synthesis of Cyclic Glycocarbonates and Acetylated Cyclic Glycocarbonates from α-Methyl Glycopyranosides In this example, cyclic glycocarbonates and acetylated cyclic glycocarbonates were synthesized from the following respective glycopyranosides: D-α-methyl mannopyranoside, D-α-methyl galactopyranoside, and D-lactose pyranose in three separate procedures. The synthetic scheme for cyclic α-methyl mannopyranoside carbonate and subsequently cyclic α-methyl mannoseopyranoside carbonate acetate is shown below in Scheme 1A:

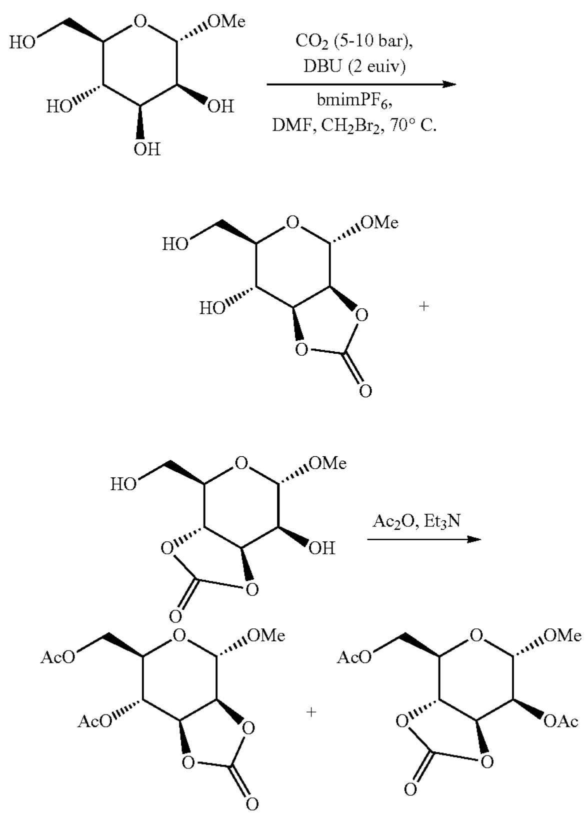

The synthetic scheme for cyclic α-methyl galactopyranoside carbonate and subsequently cyclic α-methyl galactopyranoside carbonate acetate is shown below in Scheme 1B:

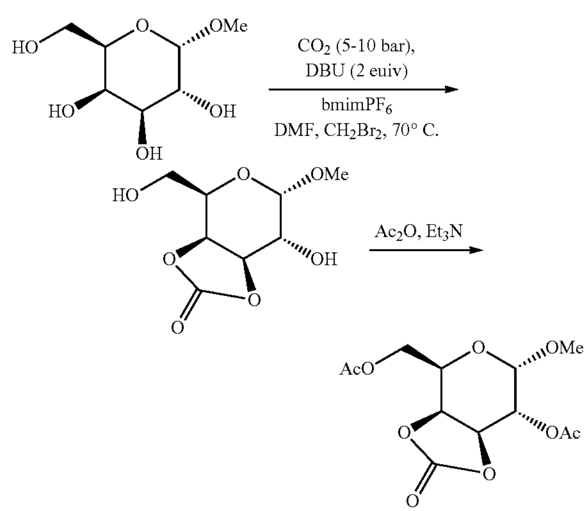

The synthetic scheme for lactopyranoside cyclic carbonate and subsequently lactopyranoside cyclic carbonate acetate is shown below in Scheme 1C:

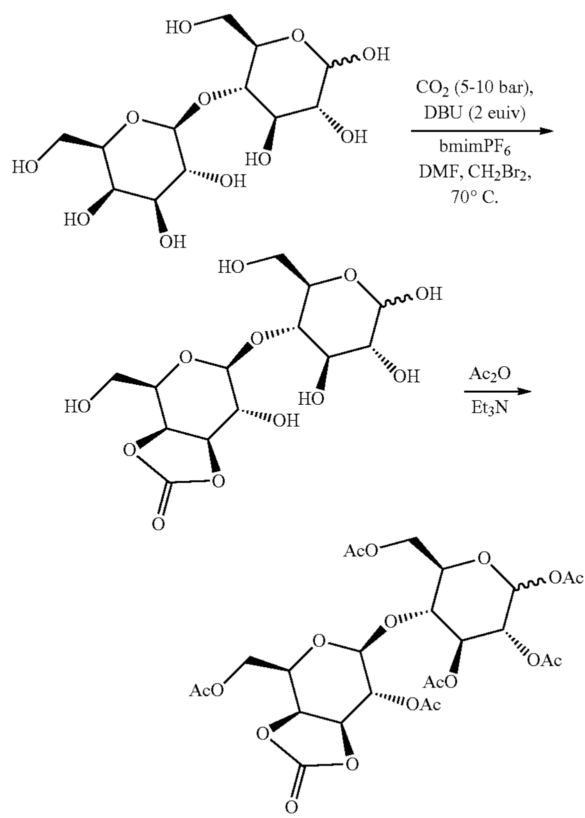

Figure 2A:
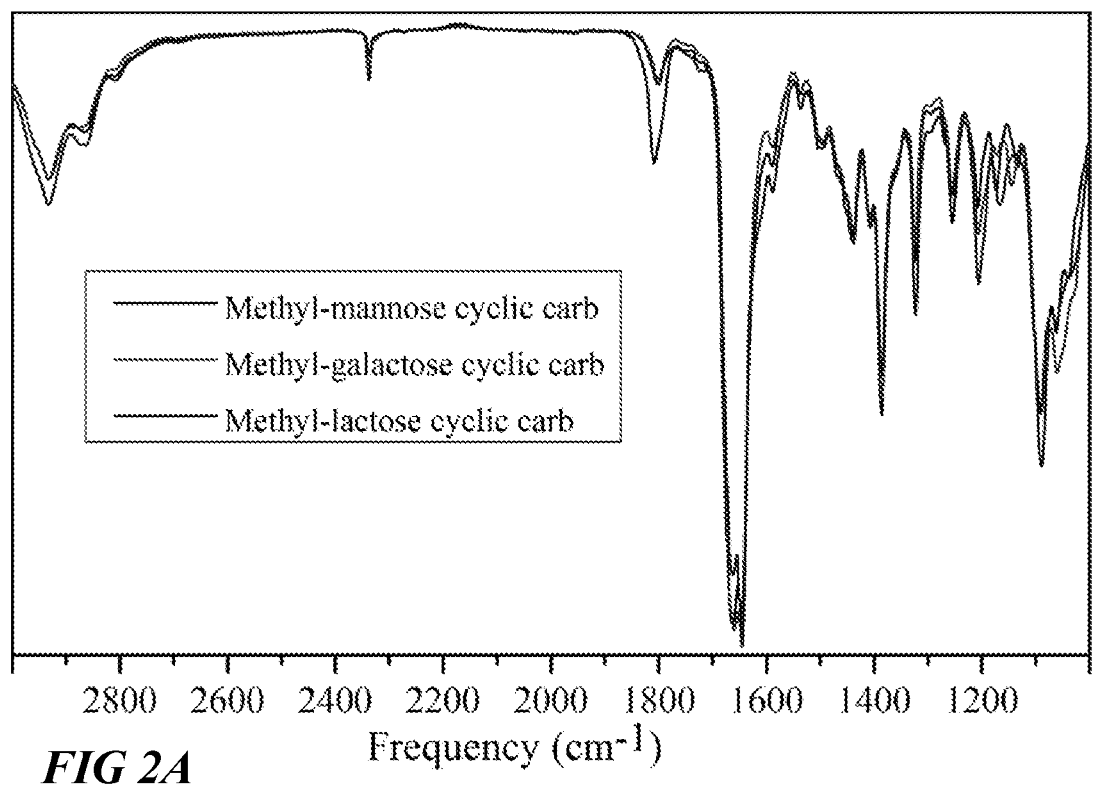
FIGS. 2A-B illustrates infrared spectra of glycocarbonates, according to one or more embodiments of this disclosure.

In each procedure, 5.15 mmol of glycopyranoside was deposited in an autoclave in addition to 2 molar equivalents (10.30 mmol) of 1,8-diazabicyclo[5.4.0]undec-7-ene (DBU) and 4 molar equivalents (20.60 mmol) of dibromomethane ($CH_2Br_2$). Next, 2 mL of dimethyl formamide (DMF) was added to the reaction mixture to solubilize the starting materials and 2 mL of ionic liquid 1-Butyl-3-methylimidazolium hexafluorophosphate ($bmimPF_6$) was added to increase the solubility of $CO_2$ in the reaction medium. The autoclave was then charged with $CO_2$ at the pressure of 5-10 bar and stirred at room temperature for 1 hour. The temperature of the autoclave was then raised to 70° C. and subsequently stirred for 20 hours, whereafter the $CO_2$ was released from the reaction mixture. The reaction products were transferred into a round bottom flask and the synthesized cyclic glycocarbonates were analyzed by infrared spectroscopy (IR). FIG. 2A illustrates the infrared spectra of each respective cyclic glycocarbonate. The peak observed at 1800 $cm^{-1}$ indicates the presence of the cyclic glycocarbonates.

Figure 2B:
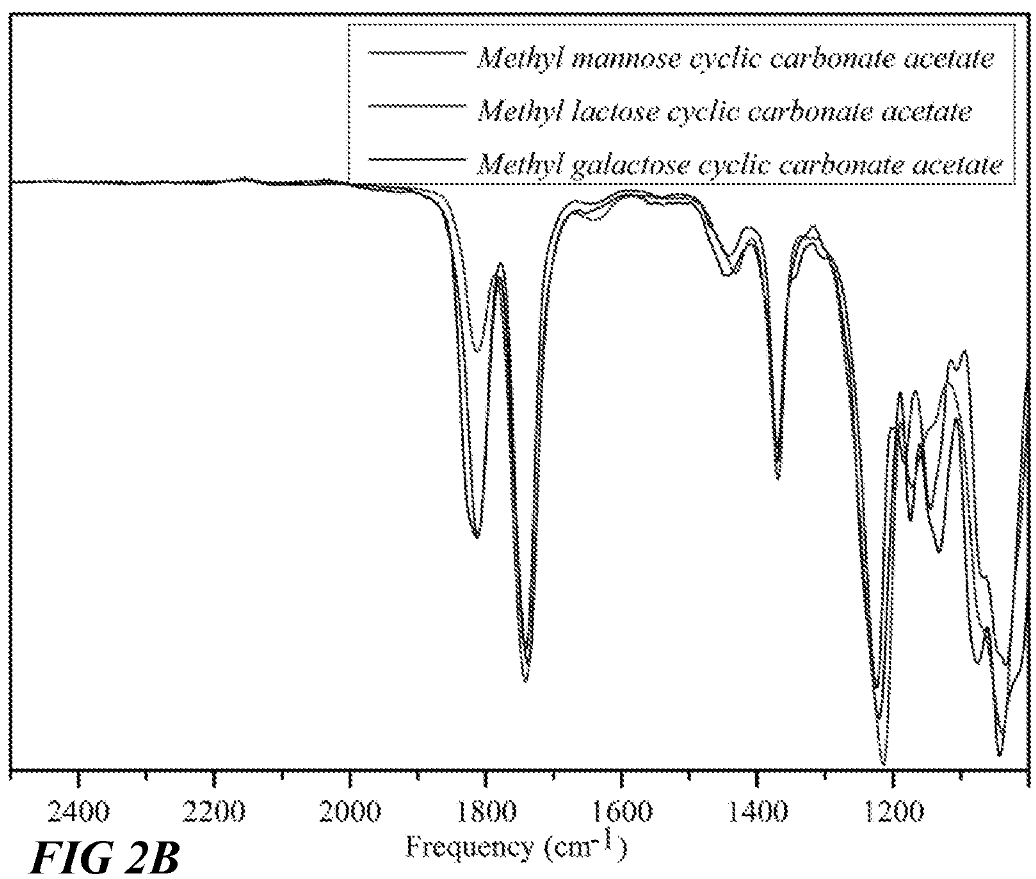

Next, 20 mL of freshly distilled anhydrous dichloromethane was added to each round bottom flask containing the cyclic glycocarbonates, along with 5 molar equivalents of trimethylamine ($Et_3N$) and 2.5 molar equivalents of acetic anhydride ($Ac_2O$). The mixtures were stirred for 12 hours to obtain the acetylated cyclic glycocarbonates. After the complete acetylation of the cyclic glycocarbonates, the reaction mixtures were washed with 1 (N) hydrochloric acid, followed by distilled water and brine solution. Finally, the reaction mixture was dried on anhydrous sodium sulphate and the solvent was removed under vacuum. The desired cyclic glycocarbonates were isolated by silica gel column chromatography purification using a 2:1 ratio of hexane and ethyl acetate (EtOAc) as the mobile phase. FIG. 2B illustrates the infrared spectra of each respective cyclic glycocarbonate acetate. The peak observed at 1800 $cm^{-1}$ further confirmed the cyclic structures.

Figure 2C:
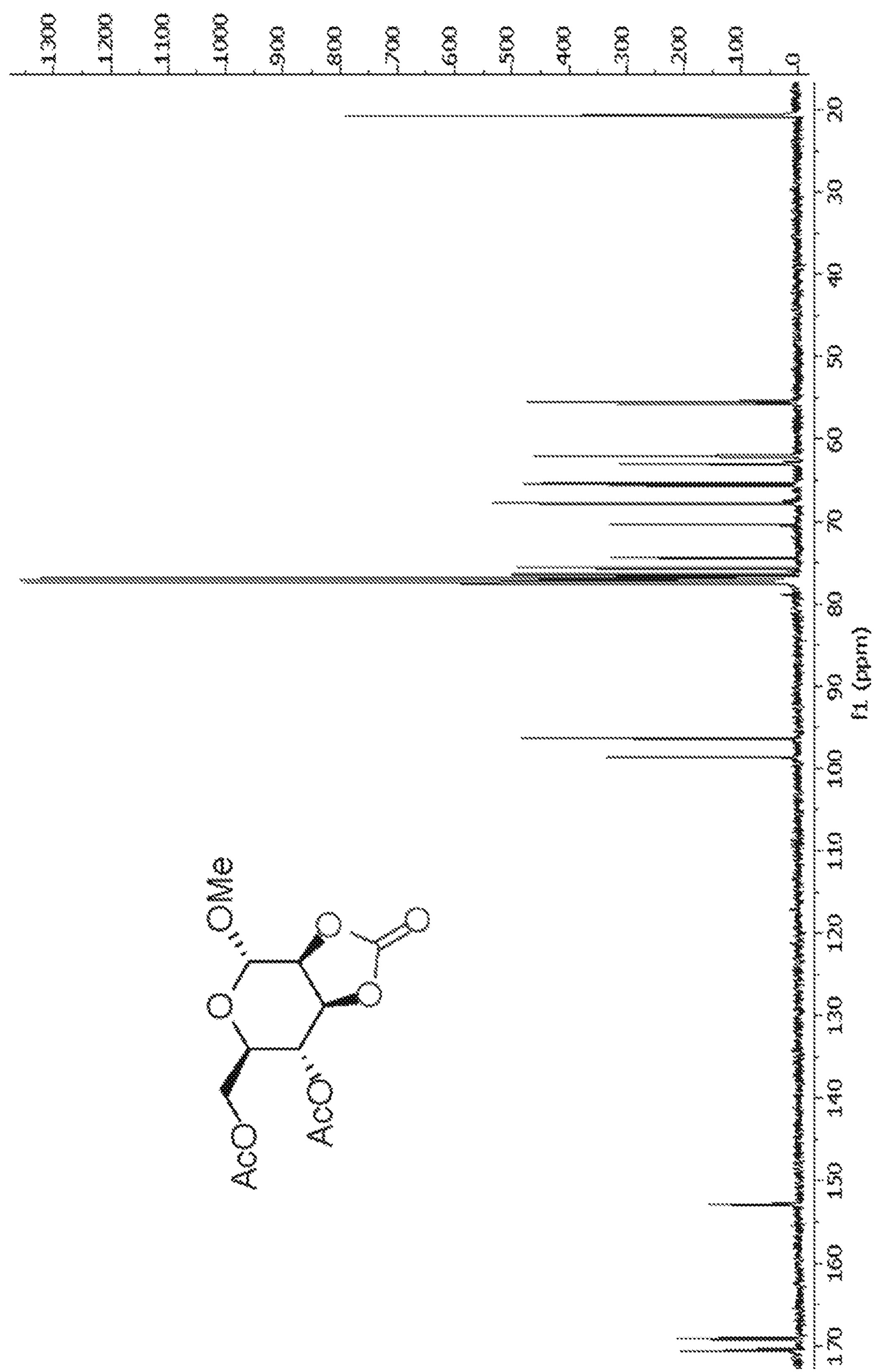
FIG. 2C illustrates a $^{13}C$ spectrum of cyclic mannose carbonate acetate, according to one or more embodiments of this disclosure.
Figure 3:
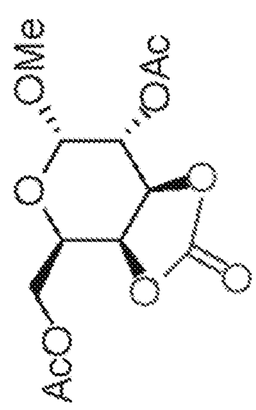
FIG. 3 illustrates a $^{13}C$ spectrum of cyclic galactose carbonate acetate, according to FIG. 4 illustrates a $^{13}C$ spectrum of cyclic Lactose carbonate acetate, according to one or more embodiments of this disclosure.
Figure 3:
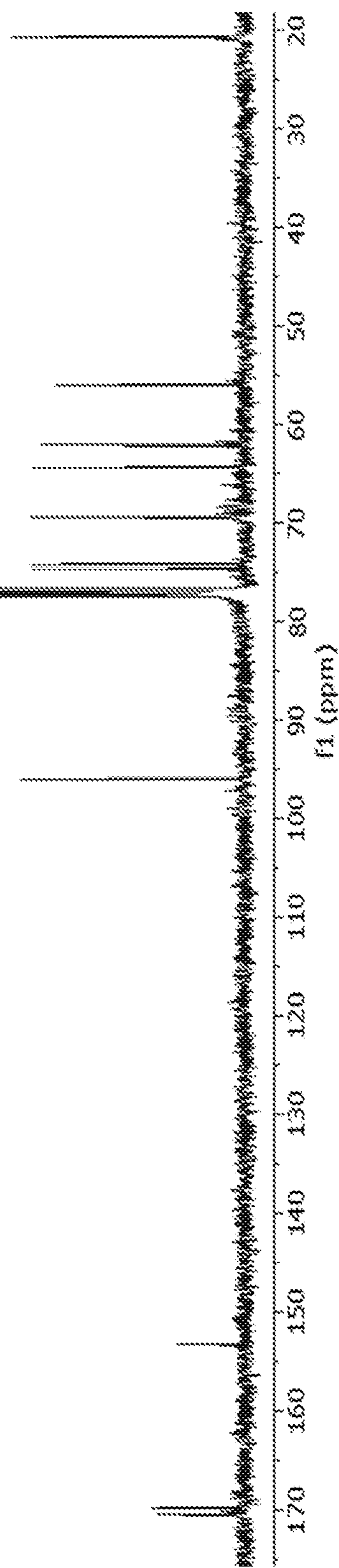

As shown in Scheme 1A, the 2 and 3 cis-hydroxyls of the methyl mannopyranoside and the 3 and 4 trans-hydroxyls of the methyl mannopyranoside underwent cyclization to produce stable cyclic carbonate with an overall 90% yield. The cyclic structure was further confirmed by H and C coupling NMR experiments. FIG. 2C illustrates a $^{13}C$ spectrum of cyclic mannose carbonate acetate. Notably, the peak at 153 ppm confirms the cyclic structure As shown in Scheme 1B, the 3 and 4 cis-hydroxyls α-methyl galactopyranoside underwent cyclization to produce stable cyclic carbonate with a 70% yield. The cyclic structure was further confirmed by H and C coupling NMR experiments. FIG. 3 illustrates a $^{13}C$ spectrum of cyclic galactose carbonate acetate. Notably, the peak at 153 ppm confirms the cyclic structure.

Figure 4:
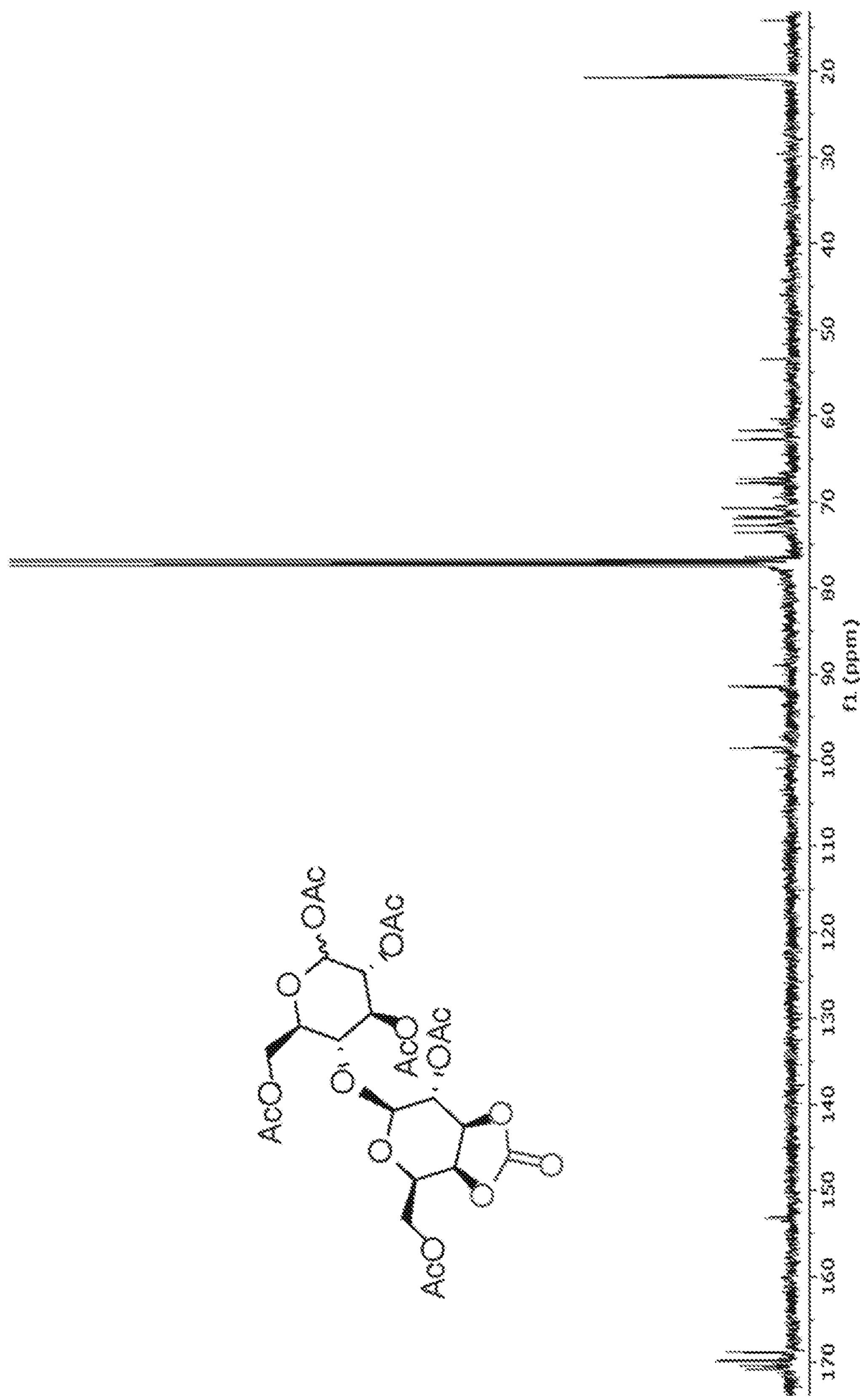

As shown in Scheme 1C, the 3 and 4 cis-dihydroxyls of the galactose moiety in the D-lactose underwent cyclization to produce cyclic carbonate with a 50% yield. The cyclic structure was further confirmed by H and C coupling NMR experiments. FIG. 4 illustrates a $^{13}C$ spectrum of cyclic Lactose carbonate acetate. Notably, the peak at 153 ppm confirms the cyclic structure.

Example 2: Synthesis of Linear Polyglycocarbonates and Acetylated Linear Polyglycocarbonates from Glucose In this example, linear polyglycocarbonates and acetylated linear polyglycocarbonates were synthesized from α-methyl glucopyranoside; the synthetic scheme is shown below in Scheme 2:

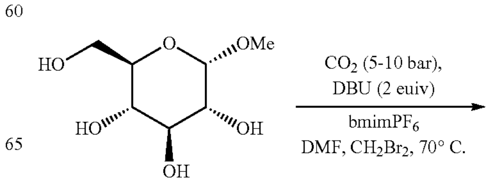

-continued

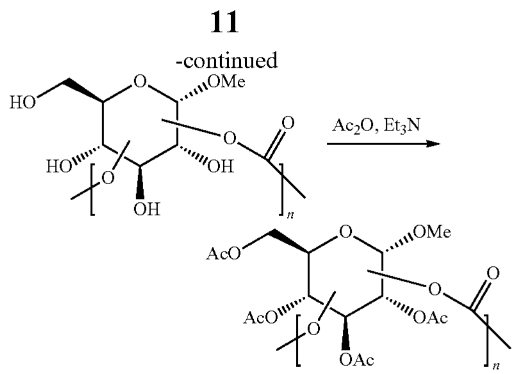

Figure 5:
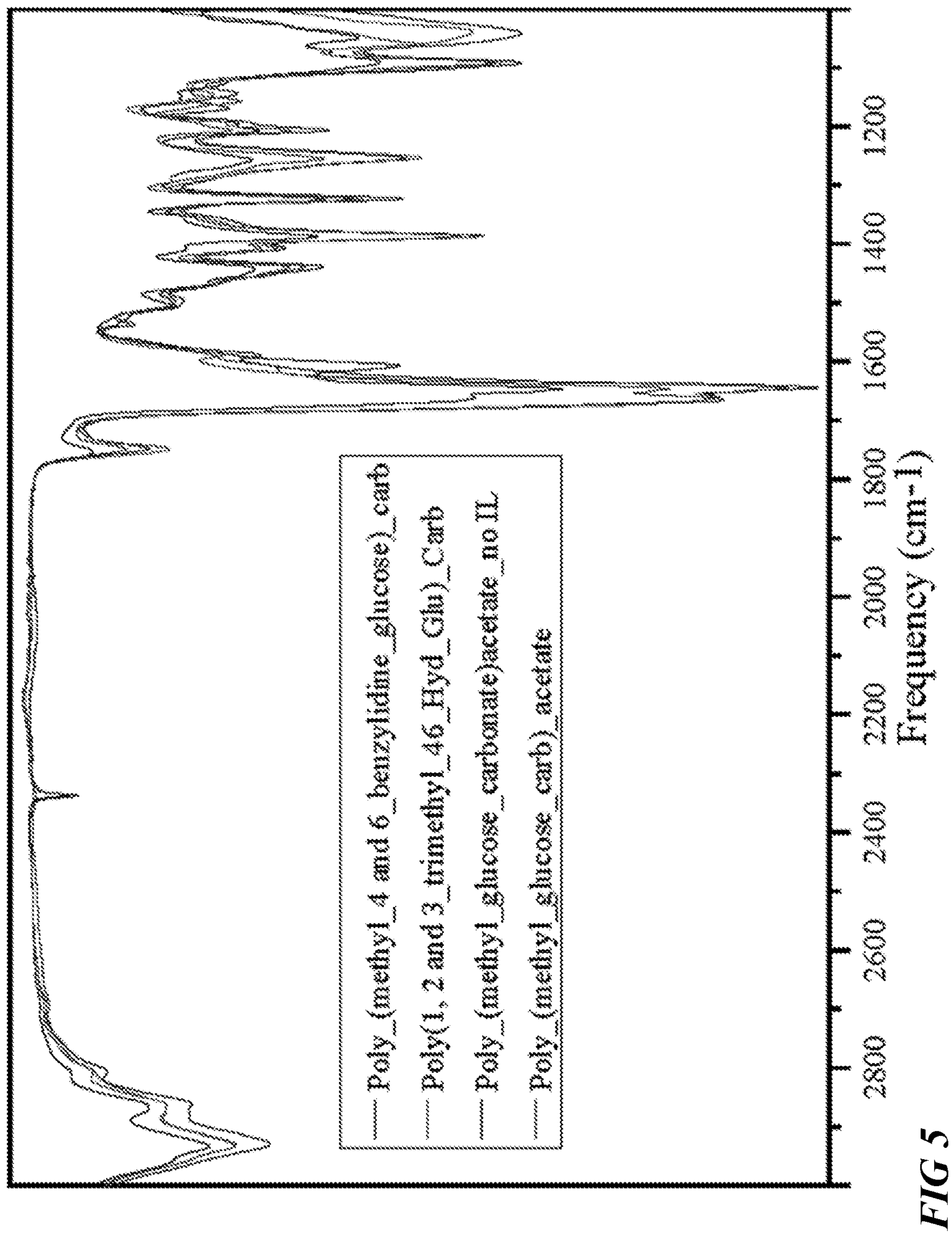
FIG. 5 illustrates an infrared spectra of linear polyglycocarbonates, according to one or more embodiments of this disclosure.

First, 5.15 mmol of α-methyl glucopyranoside was deposited in an autoclave, in addition to 2 molar equivalents (10.30 mmol) of DBU and 4 molar equivalents (20.60 mmol) of dibromomethane. Next, 2 mL of DMF was added to the reaction mixture to solubilize the starting materials. Further 2 mL of ionic liquid $bmimPF_6$ was added to increase of $CO_2$ solubility in the reaction medium. Then, the autoclave was charged with $CO_2$ at the pressure of 5-10 bar and stirred at room temperature for 1 hour. The temperature of the autoclave was raised to 70° C. and subsequently stirred for 72 hours, whereafter the $CO_2$ was released from the reaction mixture. The reaction products were transferred into a round bottom flask and the synthesized linear glycocarbonates were tested by infrared spectroscopy (IR). FIG. 5 illustrates the infrared spectra of the linear glycocarbonate. The peak observed at 1747 $cm^{-1}$ indicates the presence of the linear glycocarbonates. Because the alternating 2, 3 and 4 hydroxyls of α-methyl glucopyranoside are trans to each other, formation of linear carbonates is favored over cyclization.

Next, 20 mL of freshly distilled anhydrous dichloromethane was added to the round bottom flask containing the linear glycocarbonates, along with 5 molar equivalents of triethylamine and 2.5 molar equivalents of acetic anhydride. The mixture was stirred for 12 hours to obtain the acetylated linear glycocarbonates. After the complete acetylation of the linear polyglycocarbonates, the reaction mixture was washed with 1 (N) hydrochloric acid, followed by distilled water and brine solution was given. Finally, the reaction mixture was dried on anhydrous sodium sulphate and the solvent was removed under vacuum. FIG. 5 illustrates the infrared spectra of the synthesized acetylated linear glycocarbonates, with a peak observed at 1747 $cm^{-1}$ due to the presence of the linear glycocarbonates.

Figure 6A:
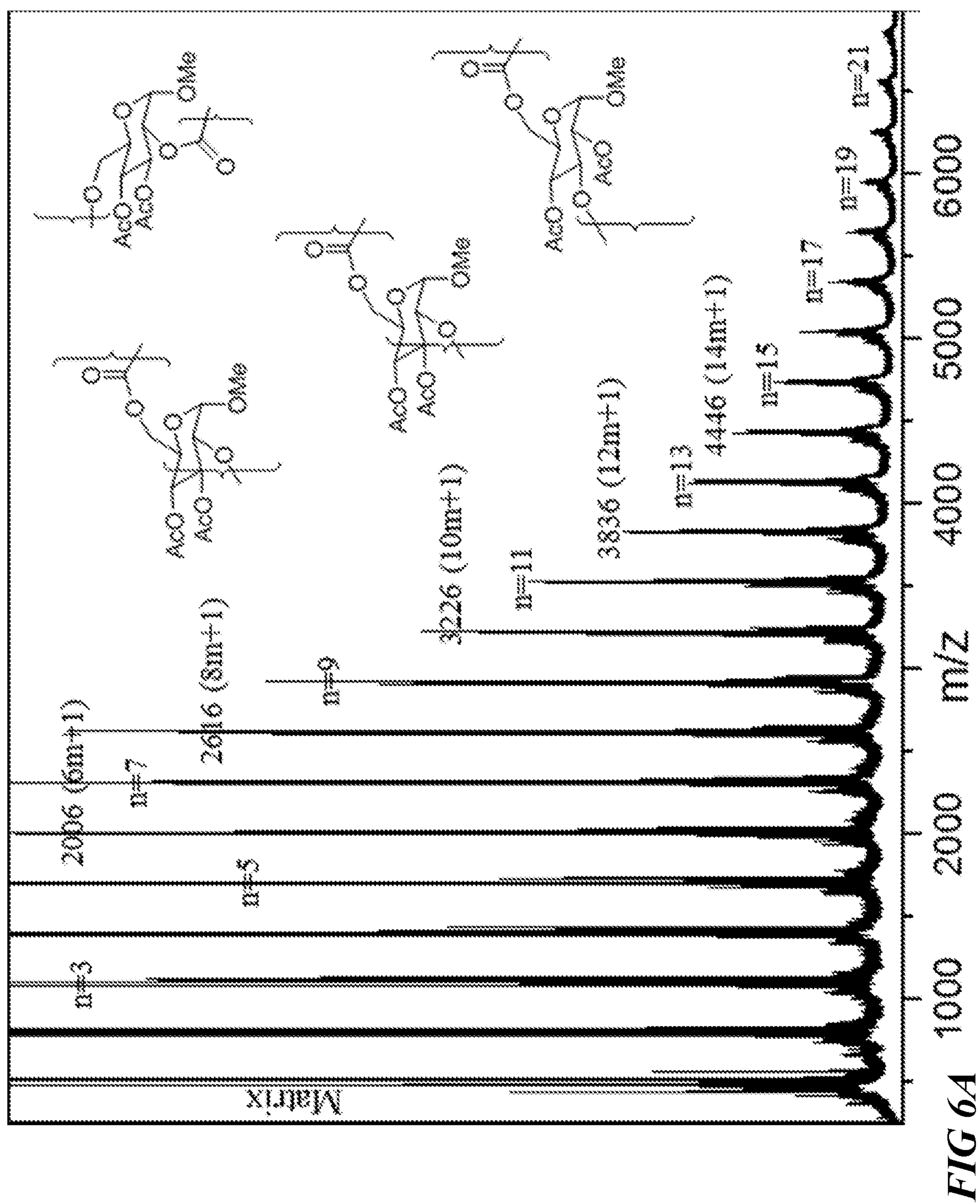
FIG. 6A illustrates MALDI-TOF data of linear polyglycocarbonate acetate, according to one or more embodiments of this disclosure.

The molecular weight and linear structure were further confirmed by H and C coupling NMR experiments. FIG. 6A illustrates MALDI-TOF data of linear polyglycocarbonate acetate in the crude reaction mixture. The results show formations ranging from small oligomeric mixtures (di, tri, tetra etc.) to higher molecular weight linear polyglycocarbonates, up to about 7 kDa. The peak to peak distance of the molecular ion peaks defines a difference of 305 Da, which is characteristic of the linear polyglycocarbonates without branching or crosslinking.

Figure 6B:
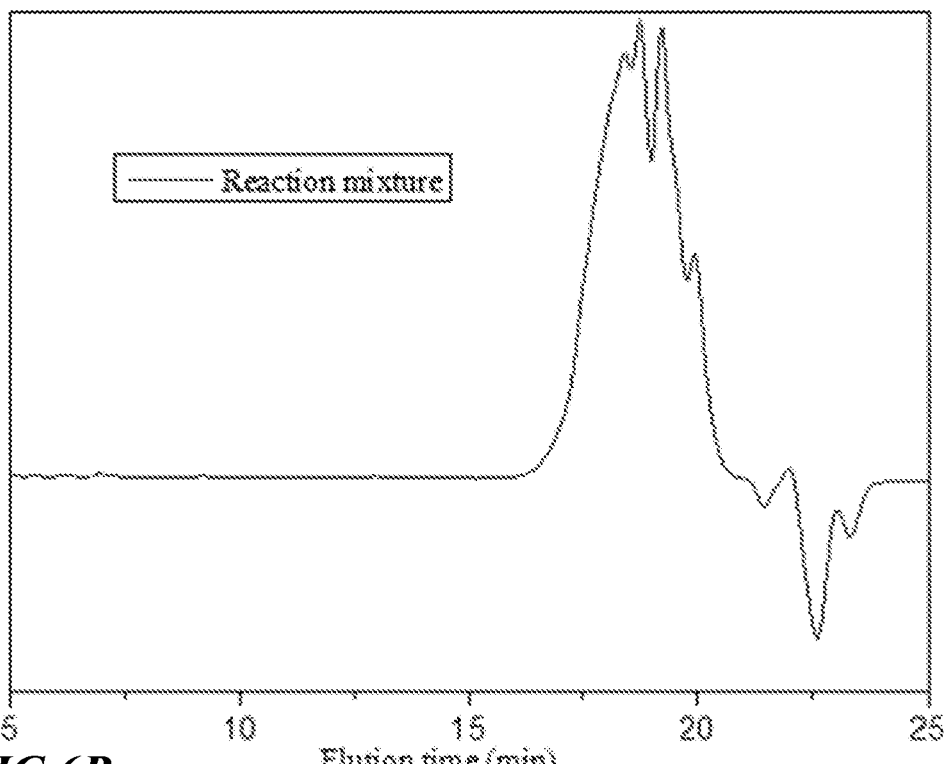
FIG. 6B illustrates a gel permeation chromatogram of linear polyglycocarbonates acetate, according to one or more embodiments of this disclosure.
Figure 6C:
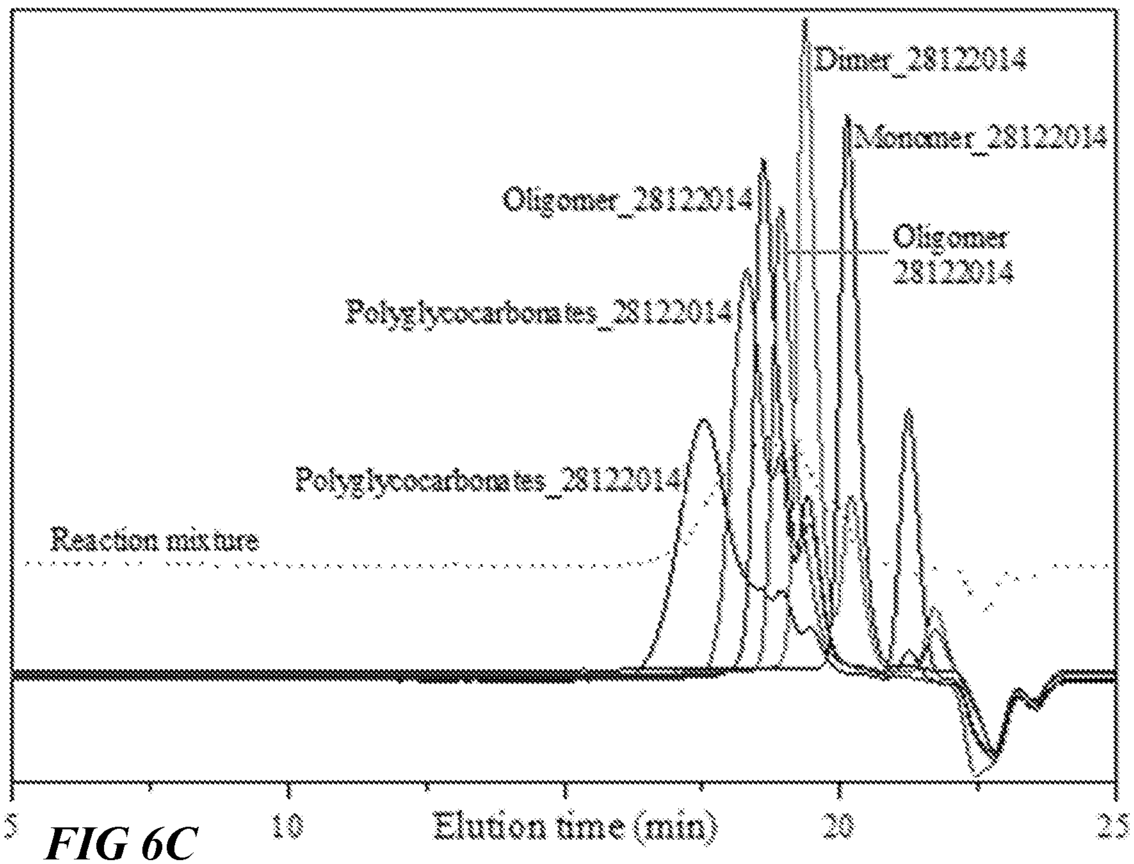
FIG. 6C illustrates a gel permeation chromatogram of oligomer small fractions from a reaction mixture, according to one or more embodiments of this disclosure.
Figure 6D:
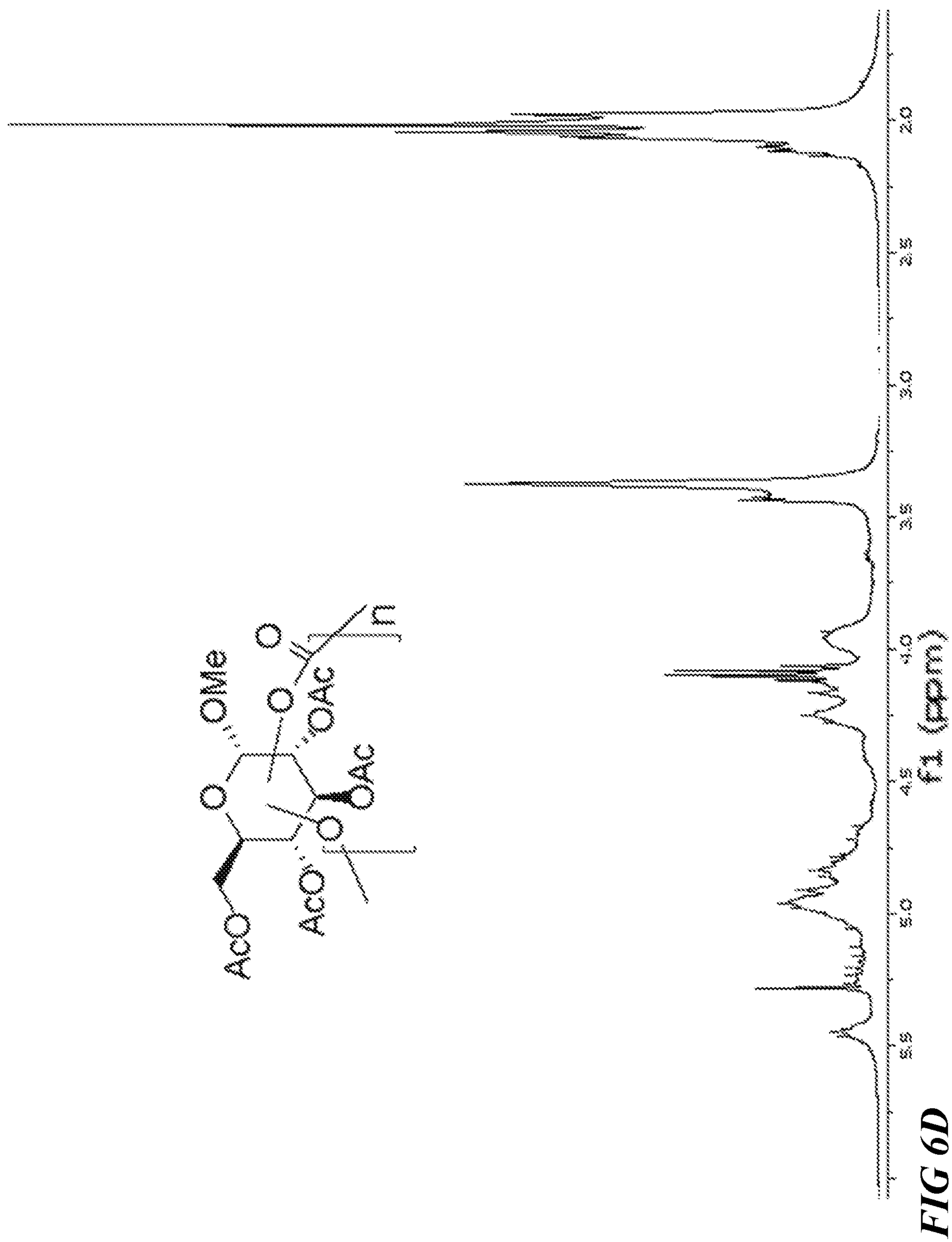
FIG. 6D illustrates a $^{1}H$ spectrum of linear polyglycocarbonate acetate, according to one or more embodiments of this disclosure.
Figure 6E:
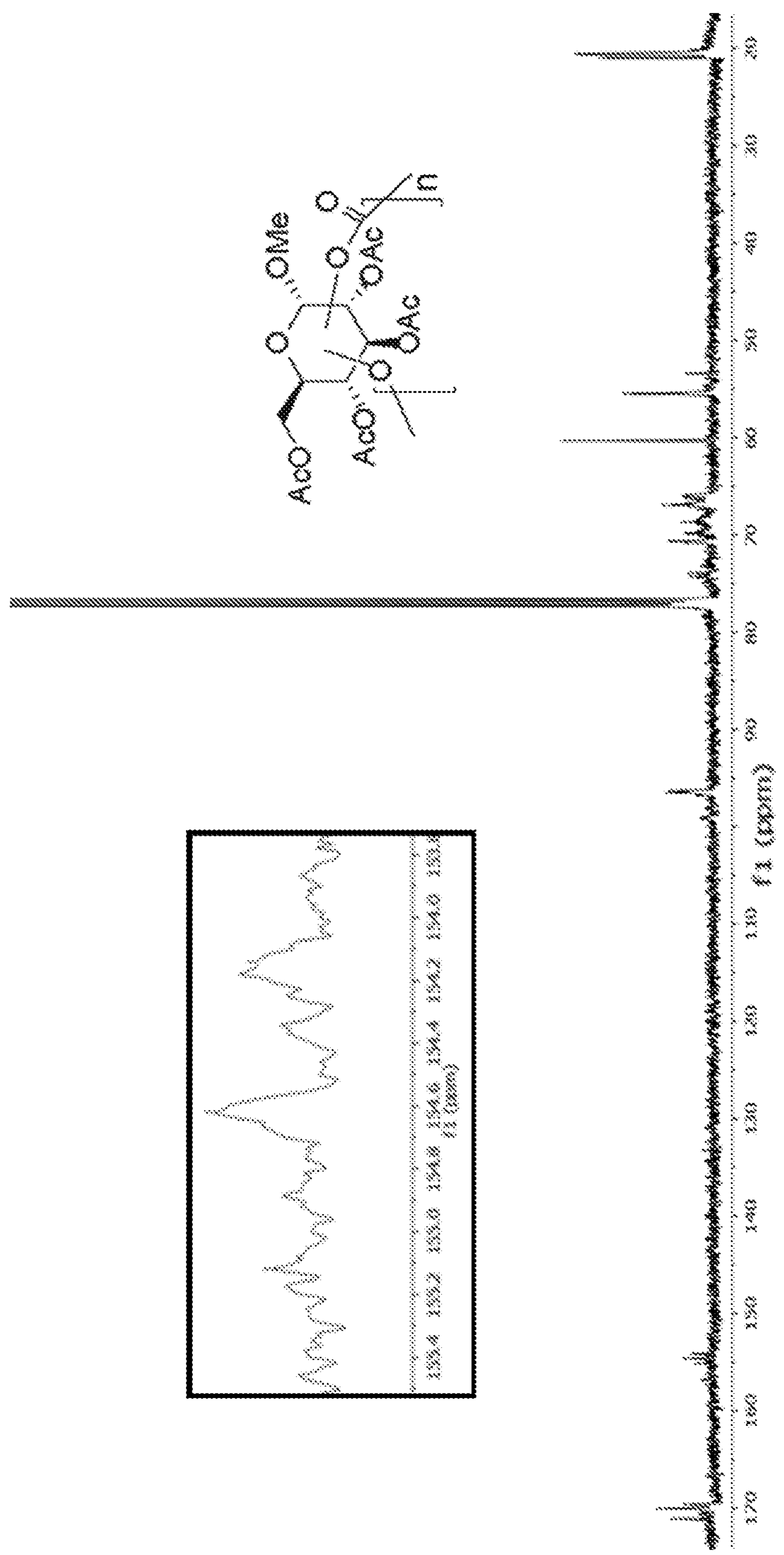
FIG. 6E illustrates a $^{13}C$ spectrum of linear polyglycocarbonate acetate, according to one or more embodiments of this disclosure.

The acetylated products of the linear polyglycocarbonates, particularly the small oligomeric mixtures (di, tri tetra etc.), were further isolated by column chromatography purification using a 2:1 ratio of hexane and ethyl acetate (EtOAc) as eluent. Further analysis was performed using GPC and $^1H$ and $^{13}C$ NMR spectroscopy. FIG. 6B illustrates a gel permeation chromatogram of the acetylated linear polyglycocarbonates. FIG. 6C illustrates a gel permeation chromatogram of oligomer small fractions from the reaction mixture. The gel permeation chromatogram showed about 90% consumption of the monomers after 72 hours. FIG. 6D illustrates a $^1H$ spectrum of the linear polyglycocarbonate acetate products. Broadened peaks were observed for the higher molecular weight polyglycocarbonates. FIG. 6E illustrates a $^{13}C$ spectrum of the linear polyglycocarbonate acetate products. Significant multi-peaks were observed at about 154-155 ppm for the mixed carbonates or oligomeric mixtures. These data confirm that the exclusively linear polyglycocarbonate reaction products contain a mixture of oligomeric and higher molecular weight polyglycocarbonates and the absence of branching and crosslinking.

Example 3: Synthesis of Linear Polyglycocarbonates from α-Methyl 4 and 6 Benzylidine 2 and 3 Dihydroxyls Glycans In this example, linear polyglycocarbonates were synthesized from α-methyl 4 and 6 benzylidine 2 and 3 dihydroxyls glycans. α-Methyl 4 and 6 benzylidine glucopyranosides were chosen as a model compound to follow the progress of the reaction where only two free hydroxyls (free 2-OH and 3-OH hydroxyls) can participate in the polycondensation reaction. The synthetic scheme is shown below in Scheme 3:

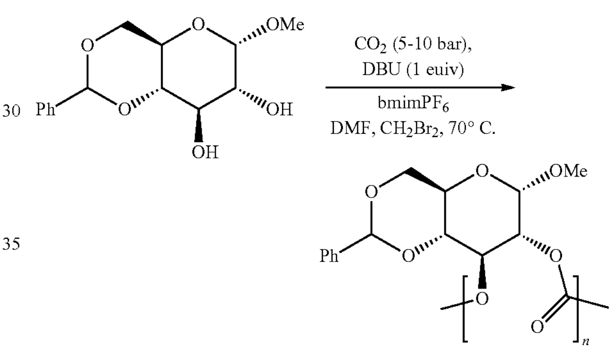

First, 3.54 mmol of α-methyl 4 and 6 benzylidine glucopyranosides was deposited in an autoclave, in addition to 1 molar equivalent (3.54 mmol) of DBU and 2 molar equivalents (7.08 mmol) dibromomethane. Next, 2 mL of DMF was added to the reaction mixture to solubilize the starting materials. Further 1 mL of ionic liquid $bmimPF_6$ was added to increase the solubility of $CO_2$ in the reaction medium. Then, the autoclave was charged with $CO_2$ at the pressure of 5-10 bar and stirred at room temperature for 1 hour. The temperature of the autoclave was raised to 70° C. and stirred for 48 hours, whereafter $CO_2$ was released from the reaction mixture. The reaction products were transferred into a round bottom flask and the synthesized linear polyglycocarbonates were tested by infrared spectroscopy (IR). FIG. 5 illustrates the infrared spectra of the linear glycocarbonate. The peak observed at 1747 $cm^{-1}$ indicates the presence of the linear glycocarbonates. The product was isolated in dichloromethane simultaneously washing with 1 (N) HCl and brine solution. The dichloromethane solution was dried over anhydrous sodium sulphate and solvent was removed under vacuum.

Figure 7A:
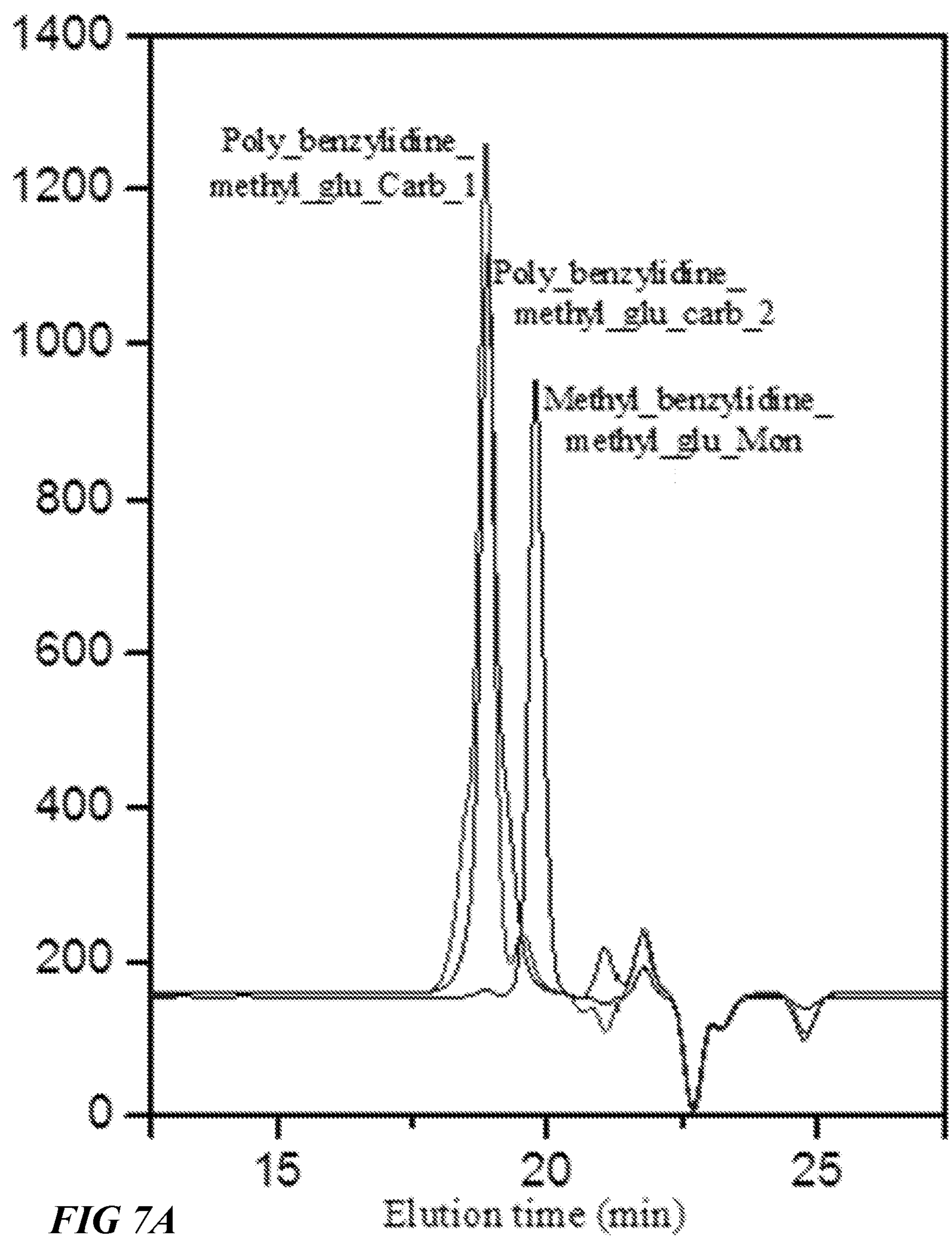
FIG. 7A illustrates a gel permeation chromatogram of Linear poly-(methyl 4 and 6 benzylidine) glucocarbonates and a α-methyl 4 and 6 benzylidine glucopyranoside monomer, according to one or more embodiments of this disclosure.
Figure 7B:
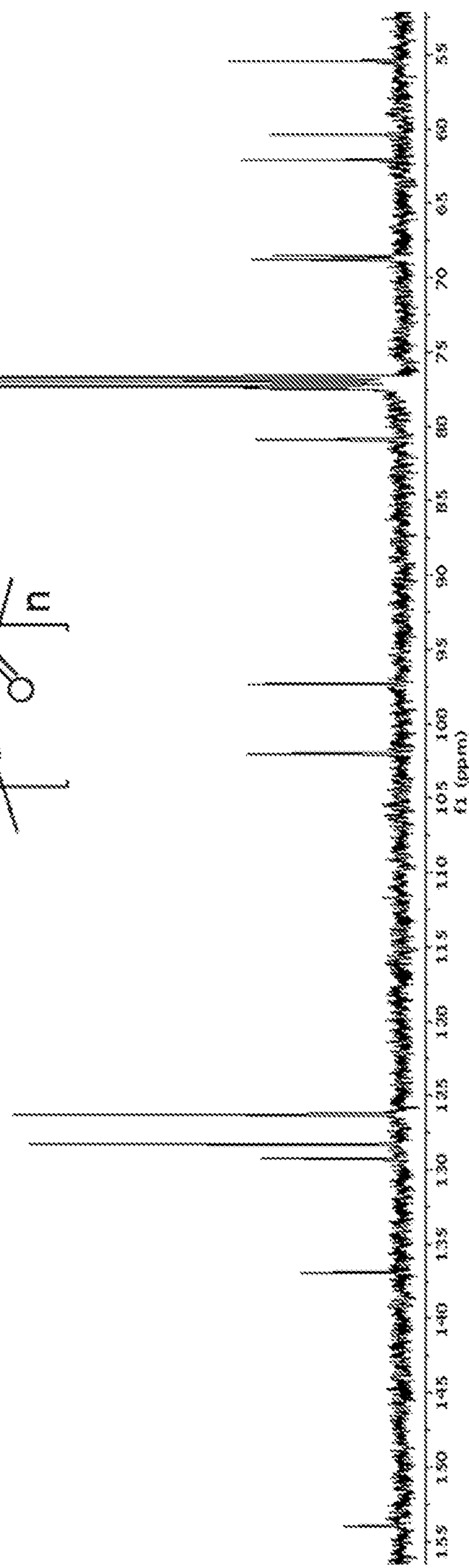
FIG. 7B illustrates a $^{13}C$ spectrum of linear poly-(methyl 4 and 6 benzylidine) glucocarbonates, according to one or more embodiments of this disclosure.
Figure 7C:
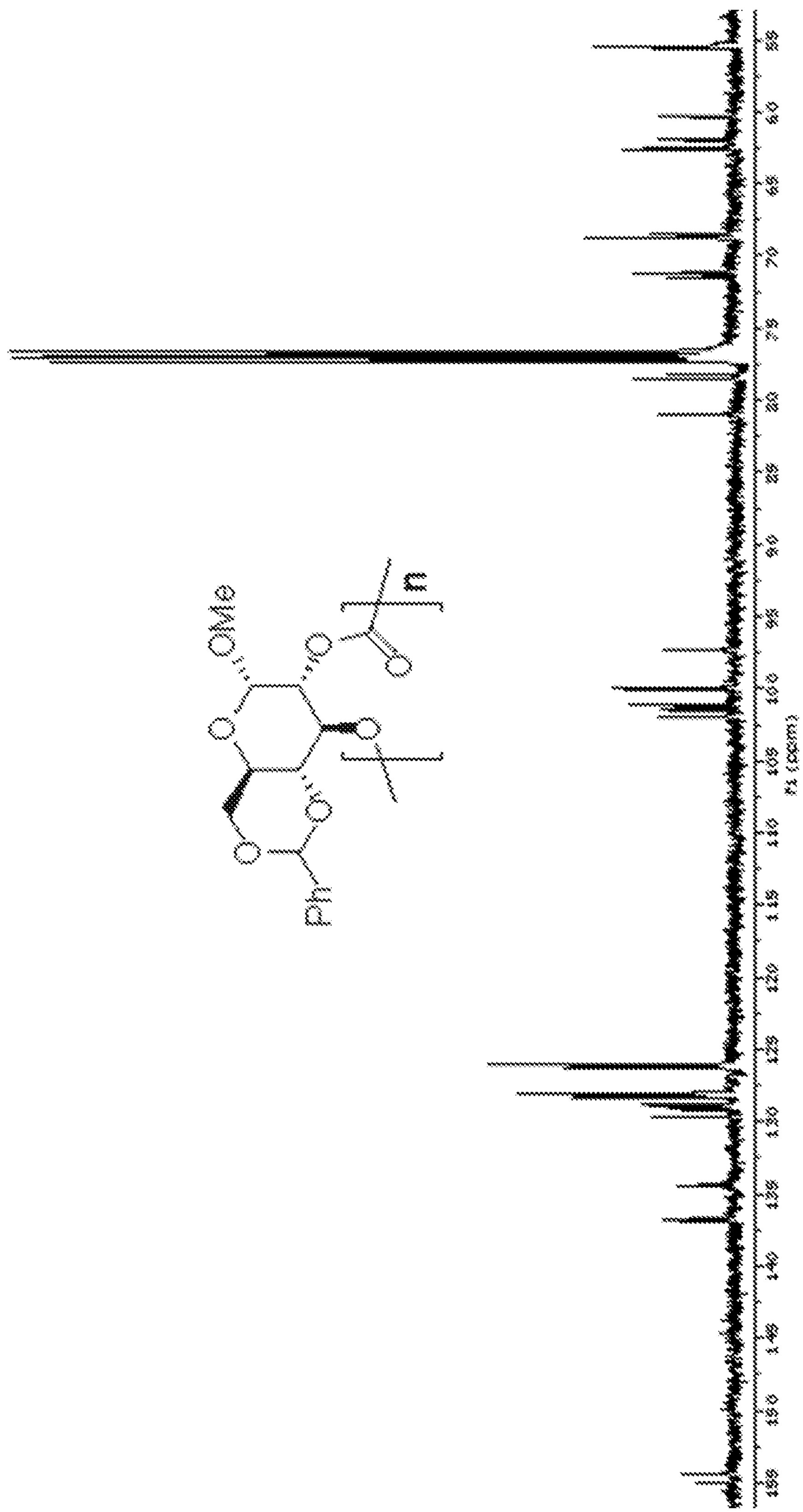
FIG. 7C illustrates a $^{13}C$ spectrum of linear poly-methyl 4 and 6 benzylidine glycocarbonates, according to one or more embodiments of this disclosure.

Following purification of the products by methods described in previous examples, the product was then characterized by GPC and $^{13}C$ NMR spectroscopy. FIG. 7A illustrates a gel permeation chromatogram of the linear poly-(methyl 4 and 6 benzylidine) glucocarbonates and α-methyl 4 and 6 benzylidine glucopyranoside monomer acetylated linear polyglycocarbonates. Although the monomer is shown to be completely consumed, the reaction did not progress to higher molecular weights. FIGS. 7B-C illustrate $^{13}C$ spectra of linear poly-(methyl 4 and 6 benzylidine) glucocarbonates. Three different 154-155 ppm $^{13}C$ peaks for the mixed carbonates are observed, indicating self-condensation of 2-OH and 3-OH and the cross condensation among 2 and 3.

Example 4: Synthesis of Linear Polyglycocarbonates from 4 and 6 Dihydroxyls Glycans Inherently, all hydroxyl substituents of a carbohydrate form a reactivity hierarchy. For example, when all hydroxyl groups attached to C-2, C-3, C-4 and C-6 in methyl-glucopyranoside have an equatorial orientation, the general order of reactivity towards nucleophilicity to form O-linkages is: 6-OH>>3-OH>>2-OH>>4-OH. Based on this concept and the disclosure herein, polycondensation can selectively be triggered by protecting specific hydroxyls. Suitable substrate glycans derivatives must 1) include a free primary hydroxyl group, and 2) a free hydroxyl at position 2, 3, or 4 (e.g., free hydroxyl groups at positions 6 and 4, positions 6 and 3, or positions 6 and 2) with all other hydroxlys protected. Scheme 4 illustrates a non-limiting list of suitable glycans with selectively available and protected hydroxyl groups:

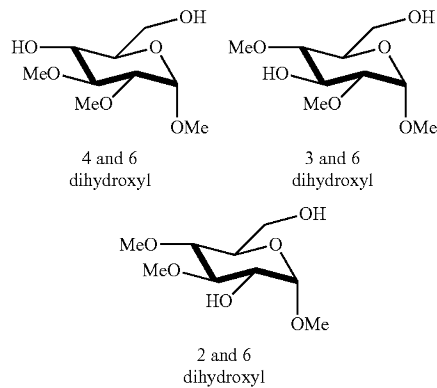

In this example, linear polyglycocarbonates are synthesized from $CO_2$ and α-Methyl 3 and 4 di-O-methyl 4 and 6 dihydroxyls glucopyranoside; the synthetic scheme is shown below in Scheme 5:

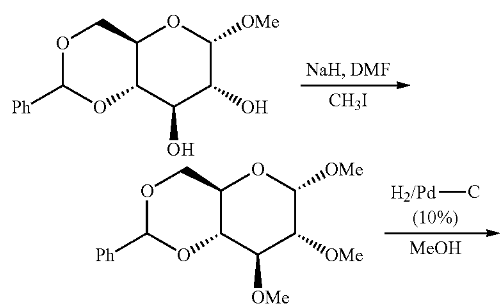

-continued

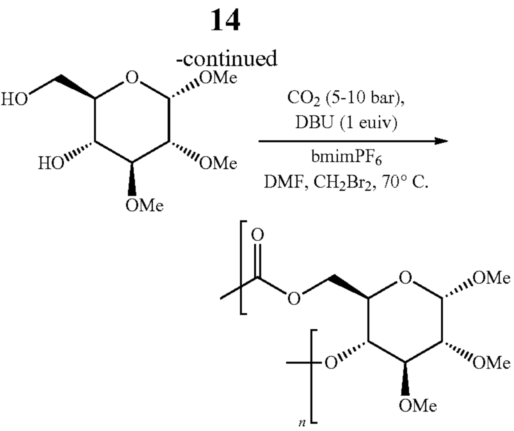

First, 7.08 mmol of α-methyl 4 and 6 benzylidine glucopyranosides was taken in a round bottom flask and 20 mL anhydrous DMF was added to the reaction mixture. Sodium hydride in 2.5 molar equivalents (17.71 mmol) was added to the reaction mixture under inert condition and stirred for 30 minutes. Next, 10 mL of DMF and 2.5 molar equivalents (17.71 mmol) of methyl iodide were added to the reaction mixture and stirred for 12 hours to obtain 1, 2 and 3 trimethyl 4 and 6 benzylidine glucopyranoside. Then the reaction mixture was diluted with dichloromethane and washed with 1 (N) HCl to remove the undesired salts. The organic layer was dried over anhydrous sodium sulfate and solvent was removed under vacuum. The compound was characterized by $^{13}C$ and $^{1}H$ NMR. The 1, 2 and 3 trimethyl 4 and 6 benzylidine glucopyranoside was hydrogenated at 30 bar hydrogen gas pressure with 10% Pd—C for 16 h in methanol to remove the bezylidine group. The completion of the reaction was confirmed by TLC and 1, 2 and 3 methyl glycopyranoside was isolated and characterized by $^{1}H$ and $^{13}C$ NMR.

Next, 4.5 mmol of α-1, 2 and 3 trimethyl glycopyranoside, 1 molar equivalent (4.5 mmol) of DBU and 2 molar equivalents (9 mmol) of dibromomethane were added to an autoclave, whereafter 1 mL of anhydrous DMF and 1 mL of bmimPF6 was added to the reaction mixture to increase the solubility of the starting materials and $CO_2$ respectively. $CO_2$ was charged to the autoclave at the pressure of 10 bar. Then the reactor was stirred for 1 hour at room temperature. Subsequently, the reaction mixture was increased to 70° C. and stirred for 48 hours. The reaction mixture was then taken from the reactor and tested with infrared spectroscopy to confirm the formation of polycarbonates. The reaction mixture was diluted with ethyl acetate and simultaneously washed with 1 (N) HCl, water and brine solution. The ethyl acetate layer was dried over anhydrous sodium sulphate and solvent was removed under vacuum. The reaction mixture was characterized by GPC, $^{1}H$ and $^{13}C$ NMR.

Figure 8A:
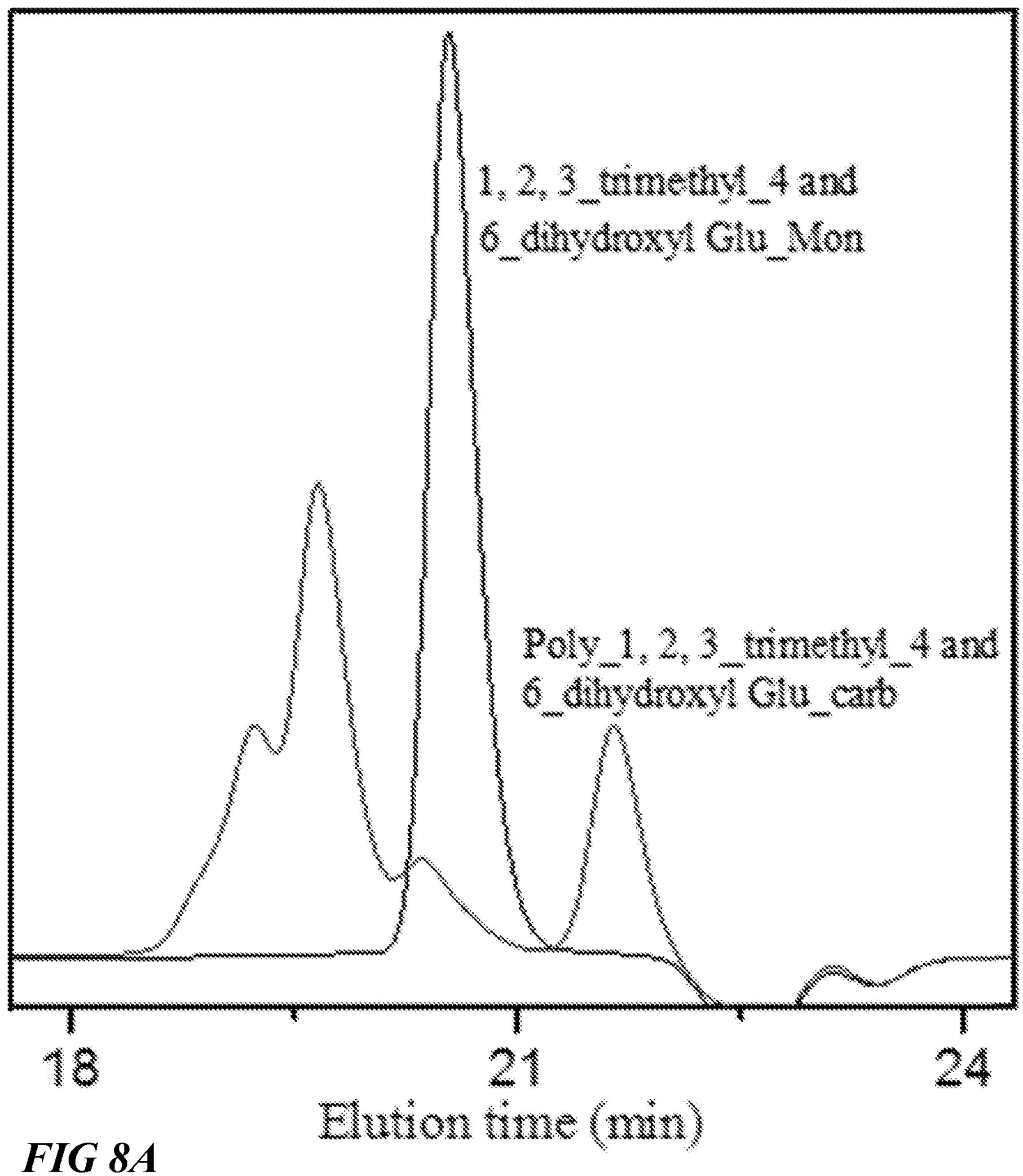
FIG. 8A illustrates a gel permeation chromatogram of Linear poly-(1,2,3-tri-O-methyl) 4 and 6 glucocarbonates and α-methyl 2 and 3 dimethyl 4 and 6 dihydroxyls glucopyranoside monomers, according to one or more embodiments of this disclosure.
Figure 8B:
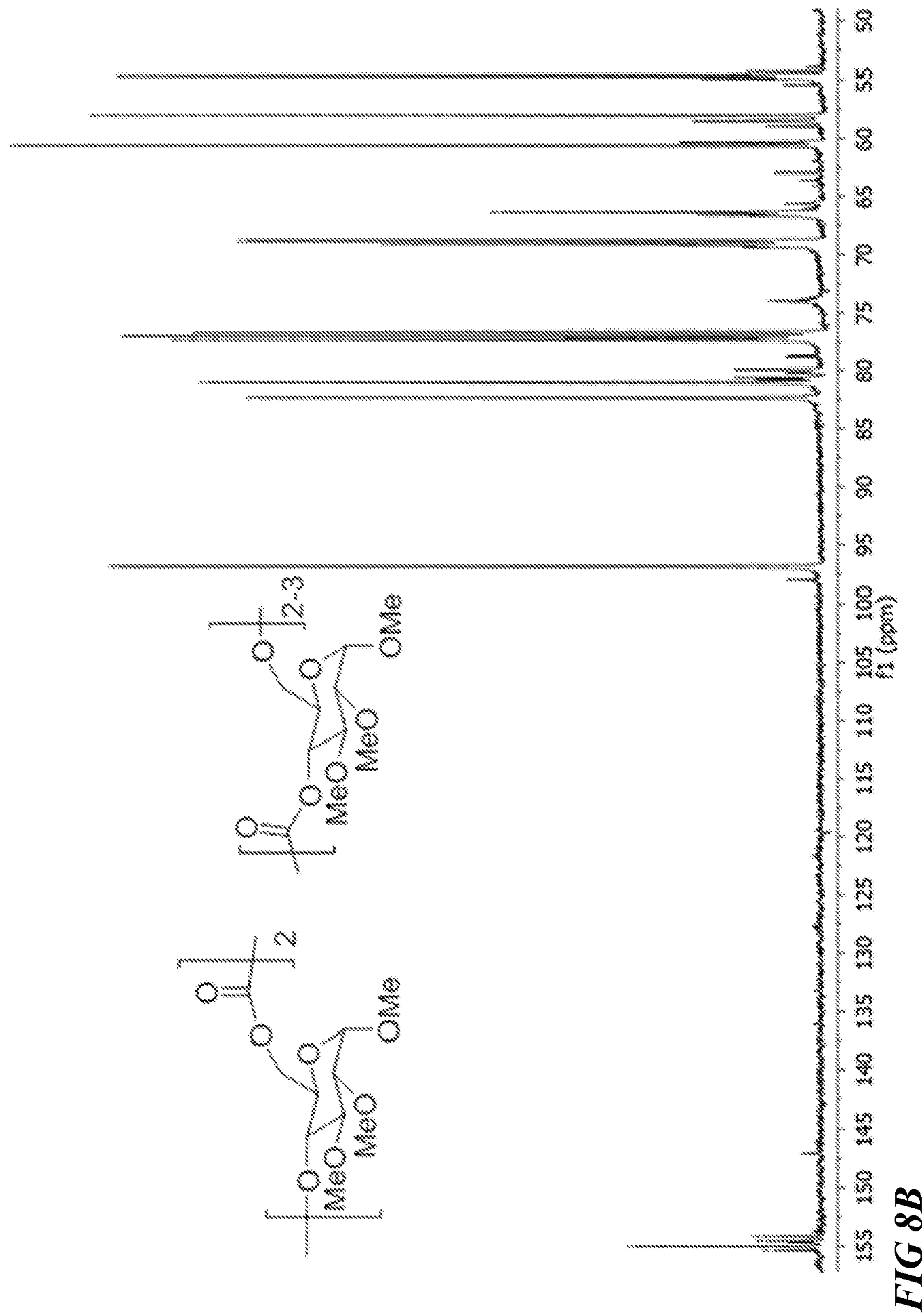
FIG. 8B illustrates a $^{13}C$ spectrum of linear poly-(methyl 3 and 4 di-O-methyl) glycocarbonates, according to one or more embodiments of this disclosure.

FIG. 5 illustrates the infrared spectra of the products, with a peak observed at 1747 $cm^{-1}$ due to the presence of the linear glycocarbonates. The reaction mixture was then purified to remove undesired components and the reaction products were analyzed by GPC and 1H and 13C NMR spectroscopy. FIG. 8A illustrates a gel permeation chromatogram of the linear poly-(1,2,3-tri-O-methyl) 4 and 6 glucocarbonates and α-methyl 2 and 3 dimethyl 4 and 6 dihydroxyls glucopyranoside monomer. Chloroform was used as eluent at the 1 mL/min flow at room temperature. The GPC results clearly show the progress of the reaction, but not to an extent of more than tetramers or oligomers, even though only a small amount of unreacted monomer could be detected in the reaction mixture. FIG. 8B illustrates the $^{13}C$ spectrum of linear poly-(methyl 3 and 4 di-O-methyl)glycocarbonates, which shows multiple peaks at about 154-155 ppm, indicating the formation of mixed carbonates.

Similar results are expected for synthesizing linear polyglycocarbonates from $CO_2$ and α-Methyl 3 and 4 di-O-methyl 2 and 6 dihydroxyls glucopyranoside, and/or α-Methyl 2 and 4 di-O-methyl 3 and 6 dihydroxyls glucopyranoside.

What is claimed is:

1. A method for making glycocarbonates, the method comprising reacting a polyol glycan with carbon dioxide, wherein the glycan comprises a closed chain structure and selected from one or more of the group consisting of hexose, a pyranose moiety, a pyranoside, and a furanose moiety, or a derivative thereof selected from the group consisting of α-Methyl 3 and 4 di-O-methyl 2 and 6 dihydroxyls glucopyranoside, α-Methyl 2 and 4 di-O-methyl 3 and 6 dihydroxyls glucopyranoside, D-α-methyl mannopyranoside, and D-α-methyl galactopyranoside.

2. The method of claim 1, wherein the polyol glycan comprises hexose.

3. The method of claim 1, wherein the polyol glycan comprises the pyranose moiety or the furanose moiety.

4. The method of claim 1, wherein the polyol glycan comprises the pyranoside.

5. The method of claim 1, wherein the polyol glycan comprises a disaccharide moiety, an oligosaccharide moiety or a polysaccharide moiety.

6. The method of claim 1, wherein the polyol glycan comprises one of the glycan derivatives selected from α-Methyl 3 and 4 di-O-methyl 2 and 6 dihydroxyls glucopyranoside and α-Methyl 2 and 4 di-O-methyl 3 and 6 dihydroxyls glucopyranoside.

7. The method of claim 1, wherein reaction occurs in the presence of one or more solvents.

8. The method of claim 7, wherein the solvents are one or more of dibromomethane, dimethylformamide, and an ionic liquid.

9. The method of claim 8, wherein the ionic liquid comprises 1-Butyl-3-methylimidazolium hexafluorophosphate.

10. The method of claim 1, further comprising selectively protecting one or more hydroxyl moieties of the polyol glycan before reacting, wherein the polyol glycan comprises at least three hydroxyl moieties.

11. The method of claim 10, wherein protecting comprises methylating.

12. The method of claim 1, wherein reacting is conducted in the presence of a catalyst.

13. The method of claim 12, wherein the catalyst comprises 1,8-diazabicyclo[5.4.0]undec-7-ene.

14. The method of claim 1, wherein the method is free of phosgene, phosgene derivatives, and isocyanates.

15. The method of claim 1, wherein reacting is conducted at a pressure between about 1 bar and about 20 bar.

16. The method of claim 1, wherein reacting is conducted at a temperature of between about 60° F. and 80° F.

17. The method of claim 1, wherein the glycocarbonates comprise linear polyglycocarbonates.

18. The method of claim 1, wherein the glycocarbonates comprise cyclic glycocarbonates.

19. The method of claim 1, wherein the hydroxyl groups forming the carbonate moiety are trans relative to each other.

20. The method of claim 1, wherein the hydroxyl groups forming the carbonate moiety are cis relative to each other.

* * * * *